United States Patent [19]

Chin et al.

[11] Patent Number: 4,522,056

[45] Date of Patent: Jun. 11, 1985

[54] METHOD AND APPARATUS FOR MEASURING REID VAPOR PRESSURE

[75] Inventors: Thomas G. Chin; Arthur Alston, both of El Cerrito, Calif.

[73] Assignee: Chevron Research Company, San Francisco, Calif.

[21] Appl. No.: 526,737

[22] Filed: Aug. 26, 1983

[51] Int. Cl.³ .............................................. G01N 7/16
[52] U.S. Cl. .................................................... 73/64.2
[58] Field of Search .................................. 73/64.2, 29

[56] References Cited

U.S. PATENT DOCUMENTS

| | | |
|---|---|---|
| 2,200,261 | 5/1940 | Carney . |
| 2,540,337 | 2/1951 | Pachaly . |
| 2,671,341 | 3/1954 | Jacobs . |
| 2,764,017 | 9/1956 | Ronnebeck . |
| 2,815,660 | 12/1957 | Rhodes et al. . |
| 2,866,339 | 12/1958 | Rhodes et al. . |
| 3,037,375 | 6/1962 | Jacobs et al. . |
| 3,191,428 | 6/1965 | Piros . |
| 3,263,491 | 8/1966 | Brown et al. . |
| 3,360,980 | 1/1968 | Webb . |
| 3,385,772 | 5/1968 | Barker et al. . |
| 3,491,585 | 1/1970 | Hass . |
| 3,499,317 | 3/1970 | Hook ............................ 73/64.2 |
| 3,528,439 | 9/1970 | Plucker . |
| 3,528,440 | 9/1970 | Plucker . |
| 3,901,062 | 8/1975 | Lynch et al. . |
| 3,937,063 | 2/1976 | Kethley . |
| 4,332,159 | 6/1982 | Chin et al. ..................... 73/64.2 |

FOREIGN PATENT DOCUMENTS 779860 11/1980 U.S.S.R. ............................ 73/64.2

Primary Examiner—Stewart J. Levy
Assistant Examiner—Joseph W. Roskos
Attorney, Agent, or Firm—Lewis S. Gruber; Edward J. Keeling

[57] ABSTRACT

A method and apparatus for measuring Reid Vapor Pressure, as defined in the ASTM D-323 procedure, of liquid hydrocarbon materials wherein a sample of material is drawn from a sample can into a sample chamber containing a bellows and then to a measuring chamber. An expansion chamber, containing a bellows, connects with a measuring chamber for adjusting the amount of air within the measuring chamber and for setting the pressure within the measuring chamber before introduction of the sample so that RVP measurement occurs at the appropriate pressure.

15 Claims, 2 Drawing Figures

FIG_2

| ELEMENT | NORMAL CONDITIONS | STEP # | 1 | 2 | 3 | 4 | 5 11 17 | 6 12 18 | 7 13 19 | 8 14 20 | 9 15 21 | 10 16 22 | 23 | 24 | 25 | 26 | 27 | 28 | 29 | 30 | 31 |
|---|---|---|---|---|---|---|---|---|---|---|---|---|---|---|---|---|---|---|---|---|---|
| | | DURATION (IN SEC.) | 2 | 5 | 10 | 2 | 1 | 5 | 5 | 5 | 5 | 5 | 2 | 15 | 120 | 3 | 5 | 2 | 1 | 10 | 180 |
| VALVE 90 | CLOSED | SAMPLE CAN AIR | | | | | | | | | | | | | | | | | | | |
| VALVE 72 | CHAMBER/DRAIN | SAMPLE IN 3-WAY | | | | | | OPEN | | | | | | OPEN | CAN/CHAMBER | | | | | | |
| VALVE 74 | OPEN | SAMPLE CYL INLET | | | | | | | CAN/CHAMBER | | | | | | | | CLOSED | | | | |
| VALVE 75 | OPEN | SAMPLE CYL OUTLET | | | | | | | | | CLOSED | | | | | | | | | | |
| BELLOWS 12 | UP | SAMPLE CYL PISTON | | | | | | | | DOWN | | | | | | | DOWN | | | | |
| VALVE 77 | CHAMBER/CHAMBER | AIR/W/CYL 3-WAY | | | | | | | | | WATER/AIR/CHAMBER 20 | | | | | | | | | | |
| VALVE 305 | AIR | AIR OR WATER 2-WAY | | | | | | | WATER | | | | | | | | | | | | |
| VALVE 306 | CLOSED | AIR & WATER 2-WAY | | | | | | | OPEN | | | | | | | | | | | | |
| VALVE 79 | OPEN | MEAS CYL INLET | | | | | | | | CLOSED | | | | | | | | | | | |
| VALVE 80 | OPEN | MEAS CYL DRAIN | | | CLOSED | | | | | | | | | | | | | CLOSED | | | |
| VALVE 81 | CLOSED | MEAS CYL CONNECT | | | OPEN | | | | | | | | | | | OPEN | | CLOSED | | | |
| BELLOWS 32 | DOWN | EXPAN CYL PISTON | | | | | | | | | | | | | | | | UP | | | |
| VALVE 83 | OPEN | EXPAN CYL OUTLET | | | | | | | | | | | | | | | | CLOSED | | | |
| VALVE 310 | CHAMBER/VENT | EXPAN CYL 3-WAY | | | | CHAMBER/AIR | | | | | | | | | | | | ON | | | |
| MOTOR 213 | OFF | SHAKER MOTOR | | | | | | | ON | | | | | | ON | | | | | ON | |

METHOD AND APPARATUS FOR MEASURING REID VAPOR PRESSURE

BACKGROUND OF THE INVENTION

The present invention pertains in general to methods and apparatus for determining vapor pressure and pertains in particular to methods and apparatus for determining the Reid Vapor Pressure (RVP) of a volatile, liquid hydrocarbon.

In internal combustion engines, fuel is transported in liquid form but burned in gaseous form. If the fuel vaporizes while it is being transported in fuel pumps, lines or carburetors, fuel flow may be decreased to the point that power loss, rough engine operation or engine stoppage results. A fuel which does not vaporize readily enough may cause hard starting, poor warm-up, poor acceleration, and unequal fuel distribution among a number of cylinders. It is therfore desirable to obtain a fuel having a characteristic volatility which provides optimal engine performance for a given ambient temperature and pressure.

One measure of volatility is the RVP. Criteria for RVP tests and apparatus have been established by the American Society for Testing Materials (ASTM) in specifications designated D-323. State regulations require that automotive gasoline meet standards established for RVP. It is therefore important for refiners of automotive gasolines to have apparatus for detemining RVP.

An invention of the present inventors which duplicates all of the essential conditions of determining ASTM D-323, and the only automatic apparatus known by the present inventors to do so, is disclosed in U.S. Pat. No. 4,332,159, and is assigned to the assignee of the present invention. The disclosure of U.S. Pat. No. 4,332,159 is hereby incorporated by reference herein.

Other than the device disclosed in U.S. Pat. No. 4,332,159, automated devices known to the present inventors deviate from ASTM D-323 to the extent that their results must be correlated with RVP. Correlation error inherent in such results makes them less likely to be accurate than results obtained by direct measurement. Thus, a particular advantage of the apparatus of U.S. Pat. No. 4,332,159 is the fidelity with which RVP is measured. However, seals, such as those located around pistons used in the apparatus in U.S. Pat. No. 4,332,159 are subject to leakage and consequently reduce reliability.

SUMMARY OF THE INVENTION

Accordingly, it is an object of the present invention to provide a new and improved apparatus for measuring the RVP of a liquid hydrocarbon material.

It is a further object of the present invention to provide a new and improved method for measuring the RVP of a liquid hydrocarbon material.

Among the advantages of the present invention is that it eliminates the need for sliding seals to handle test fluids and, consequently, eliminates piston leakage problems.

These and other objects and advantages of the present invention will become apparent to those skilled in the art upon consideration of the accompanying specification, claims and drawings.

In order to attain the above-mentioned and other objects and advantages, the apparatus of the present invention measures the RVP of a liquid hydrocarbon material. The apparatus comprises a first compartment maintained at a substantially fixed temperature in about the range of 32° F. to 40° F. A second compartment is maintained at a substantially fixed temperature of about 100° F. Means, within the first compartment, provide a sample of the liquid hydrocarbon material to a sample chamber in the first compartment by way of a first means for connecting. The sample chamber is connected to a measuring chamber within the second compartment by a second means for connecting. An expansion chamber within the second compartment is connected by a third means for connecting the measuring chamber. Means for measuring pressure associated with the measuring chamber are coupled to means for providing an output indicative of the vapor pressure of the sample of the liquid hydrocarbon material.

A method for measuring RVP of a liquid hydrocarbon material according to the present invention involves filling the sample chamber at a temperature within the range of about 32° F. to about 40° F. with a sample of the liquid hydrocarbon. The measuring chamber, having a volume of 5 $V_S$, is prepared at about 100° F. and atmospheric pressure. The measuring chamber is connected to an expansion chamber and then the expansion chamber is expanded to establish a total volume within the measuring chamber and the expansion chamber of about 6.25 $V_S$. The measuring chamber is disconnected from the expansion chamber. A sample volume, $V_S$, of the liquid hydrocarbon is transferred from the sample chamber to the measuring chamber and equilibrium pressure within the measuring chamber is measured as the RVP of the sample.

BRIEF DESCRIPTION OF THE DRAWINGS

FIG. 2 is a chart illustrating the operating sequence and duration of operation for elements of the apparauts of FIG. 1.

DESCRIPTION OF THE PREFERRED EMBODIMENT

Figure 1:
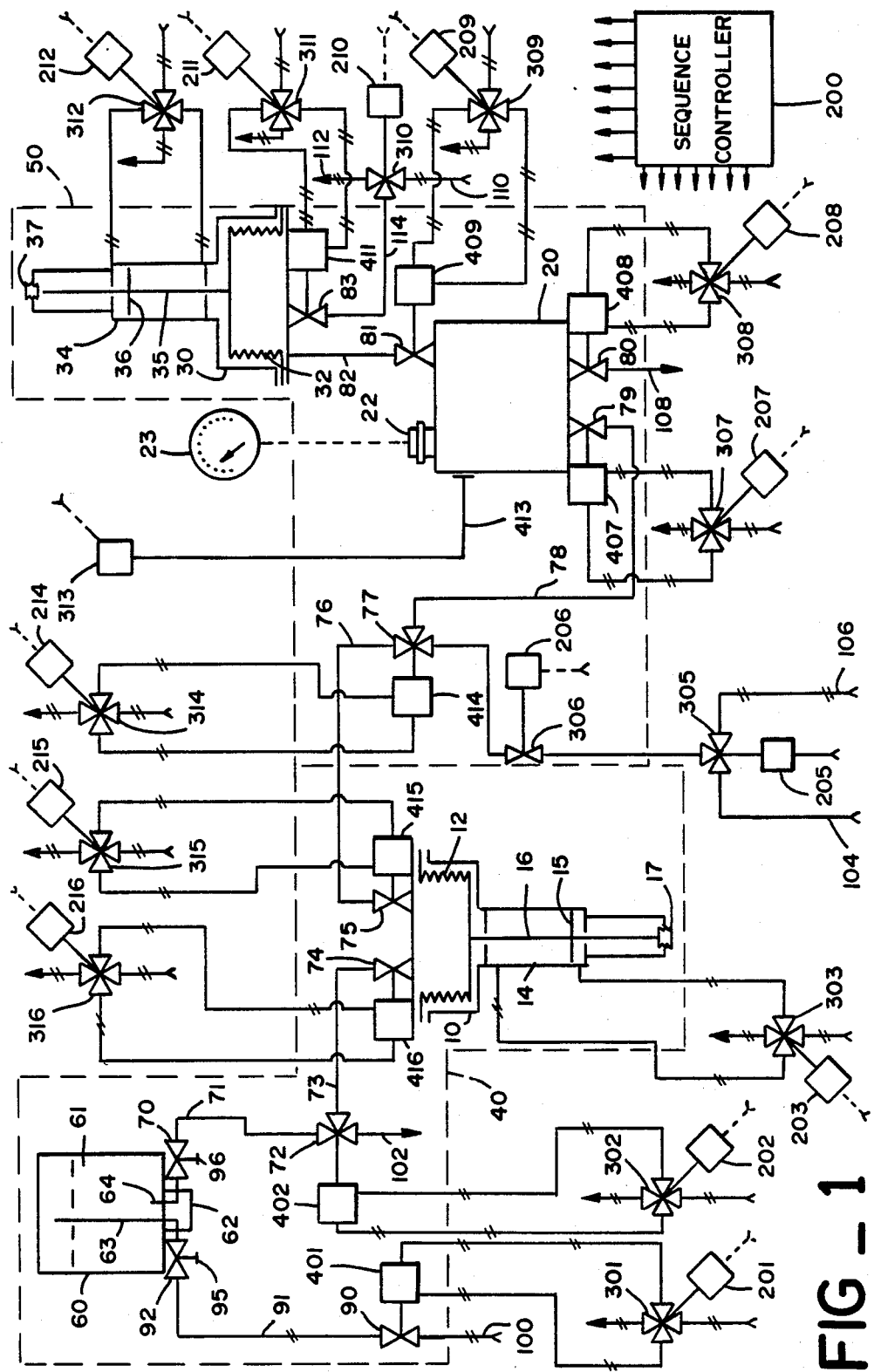
FIG. 1 is a schematic diagram of an apparatus according to the present invention.

A preferred embodiment of the apparatus of the present invention, as illustrated in FIG. 1, is intended to function according to the procedure established by ASTM D-323. A sample chamber is maintained within a first compartment 40 at a temperature within the range of about 32° F. to about 40° F. The sample chamber is filled with a chilled sample of a liquid hydrocarbon material. This sample is than transferred to an air chamber in the form of a measuring chamber 20 which is maintained within a second compartment 50 at a constant temperature of about 100° F. Measuring chamber 20 is shaken until a liquidvapor equilibrium is attained within chamber 20. The vapor pressure within chamber 20 is measured by means of a pressure sensor 22 the output of which is read on a gauge 23.

In order to comply with ASTM D-323, the sample of the liquid hydrocarbon is obtained and prepared according to the specifications therein. A chilled sample within a sample can 60 is then introduced within compartment 40 in order to begin the test. After a test, measuring chamber 20 and all connecting tubes between sample chamber 10 and measuring chamber 20 are purged by flushing with water and air to remove any residual sample. A sequence controller 200 supplied signals which control all of the operations necessary to perform the steps of the test for RVP as carried out by the apparatus according to the present invention.

In a conventional technique for measuring RVP in accordance with ASTM D-323, a sample container and a measuring container are connected to form a combined volume in which pressure is measured. Because the opened measuring container is warmed in a water bath at 100° F., it contains water-saturated air. This water-saturated air is retained in the combined volume during pressure measurement. These conditions are duplicated in the present invention by flushing measuring chamber 20 with water, so that the air within measuring chamber 20 is saturated with water. Also, by temporarily expanding the volume of measuring chamber 20 into an expansion chamber 32, air, which would otherwise be in a greater amount and at a higher pressure than in conventional techniques due to compression by an introduced sample, is maintained at an appropriate pressure and in an appropriate amount for RVP measurement.

For solid lines linking elements in FIG. 1, all upward pointing arrows correspond to vents, all downward pointing arrows correspond to drains and all tails of arrows correspond to sources. Lines crossed by slash marks correspond to lines dedicated to an air supply system.

Within first compartment 40 sample can 60 contains a liquid hydrocarbon material 61 to be sampled. Sample can 60 is attached to an adaptor 62 through which pass an air conduit 63 and a liquid conduit 64. Conduit 63 is connected to a first port of a valve 92 having a shut-off knob 95. A second port of valve 92 is connected to an air line 91 which is in turn connected to a first port of a valve 90. A second port of valve 90 is connected to an air supply valve 100. Conduit 64 is connected to a first port of a valve 70 having a shut-off knob 96. A second port of valve 70 is connected to conduit 71 which in turn is connected to a first port of a valve 72.

A second port of valve 72 is connected to conduit 73 while a third port of valve 72 is connected to a drain line 102. Conduit 73 is also connected to a first port of a valve 74 which has a second port connected to an inlet of sample chamber 10.

Sample chamber 10 contains a bellows 12 into the cavity of which the second port of valve 74 opens. A piston actuator 14 is connected to bellows 12 by way of a first end of rod 16. Rod 16 is in turn connected to a piston 15 within a piston actuator 14. The travel of a second end of rod 16 is liminted by a stop 17 passing through a surface of actuator 14.

A valve 75 has a first port connected to the cavity of bellows 12 and it has a second port connected to a conduit 76. Conduit 76 is also connected to a first port of a valve 77 which has a second port connected to a conduit 78 and a third port connected to a first port of a valve 306. A second port of valve 306 is connected to a conduit which is in turn connected to a first port of a valve 305. A second port of valve 305 is connected to an air supply line 106. A third port of valve 305 is connected to a water supply line 104.

Conduit 78 connects the second port of 77 with a first port of a valve 79. A second port of valve 79 is connected to an inlet of measuring chamber 20. A first outlet of measuring chamber 20 is connected to a first port of valve 80, a second port of which is connected to a drain line 108.

A second outlet of measuring chamber 20 is connected to a first port of a valve 81, a second port of which is connectd to a conduit 82. Conduit 82 connects the second port of valve 81 with an inlet of expansion chamber 30, which inlet opens into a cavity of bellows 32. Bellows 32 is connected to a rod 35. Rod 35 is in turn connected to a piston 36 within an actuator 34. The travel of rod 35 within actuator 34 is limited by a stop 37 passing through a surface of actuator 34 at one end of rod 35. A first port of a valve 83 is connected to an opening to the cavity of bellows 32 while a second port of valve 83 is connected by way of a conduit 114 to a first port of a valve 310. A second port of valve 310 is connected to an air supply 110 while a third port of valve 310 is connected to a vent line 112.

Because the apparatus of the present invention is designed so that the sample can, sampling chamber, and measuring chamber may be submerged in liquid, all of the valves within compartments 40 and 50 are pneumatically actuated. As is clear to one skilled in the art, pneumatic actuation of valves is not an essential feature of the present invention but is merely a feature of the operating environment of the preferred embodiment.

The sequence of the operations performed within the apparatus of FIG. 1 is determined by sequence controller 200 which changes the position of valves within compartments 40 and 50 through the action of solenoids upon valves directing air supply to opposing input lines of pneumatic actuators.

Specifically, a solenoid 201 operates a valve 301 controlling an actuator 401 which in turn operates valve 90. A solenoid 202 operates a valve 302 which controls an actuator 402 to operate a valve 72.

A solenoid 203 operates a valve 303 to alternately switch an air supply from connection with a vent to either side of piston 15 in order to move piston 15 toward bellows 12 or away from bellows 12. A solenoid 205 controls valve 305 and a solenoid 206 controls valve 306.

A solenoid 207 controls a valve 307 which directs an actuator 407. Actuator 407 operates valve 79. A solenoid 208 operates a valve 308 to control an actuator 408 to operate valve 80. Similarly, a solenoid 209 controls valve 309 to direct an actuator 409 which operates valve 81.

A solenoid 210 operates valve 310. A solenoid 211 operates a valve 311 to control an actuator 411 which opertes valve 83. A solenoid 212 operates a valve 312 to either connect or disconnect an air supply line from a vent. Valve 312 also connects the air supply line either above or below piston 36 in order to move piston 36 either toward or away from bellows 32.

An electric switch within a shaker motor 313 is controlled by sequence controller 200 to operate a crank and arm mechanism 413. A solenoid 214 operates a valve 314 to control an actuator 414 to operate valve 77. Likewise, a solenoid 215 operates a valve 315 to control an actuator 415 to operate valve 75. A solenoid 216 operates a valve 316 to control an actuator 416 to operate valve 74.

Solenoids 201, 202, 203, 205, 206, 207, 208, 209, 210, 211, 212, 214, 215 and 216 and motor 313 all are connected to and controlled by sequence controller 200. Each of valves 301, 302, 303, 307, 308, 309, 311, 312, 314, 315 and 316 connects an air supply line with a vent unless switched to control a corresponding actuator.

Valves, solenoids, pressure sensors and gauges, pneumatic actuators, piston actuators, sequence controllers and other components of the present invention are well known and readily available to those skilled in the art.

Readily available metal bellows are employed in the sampling and expansion chambers of the present invention.

Before a sample flows into sample chamber 10, bellows 12 is in a compressed position. When a compressing force, applied by rod 16, is removed so that a sample can be drawn into chamber 10, bellows 12 must be restrained from opening too fast in order to avoid undesirable vaporization. A spring or other restraining device may be used to slow the expansion of bellows 12.

Tubing which carries sample to measuring chamber 20 should have a small diameter and be as short as possible consistent with the length needed to accommodate the shaking of chamber 20. This tubing should also be insulated from the 100° F. temperature of compartment 50 in order to reduce the chance of sample vaporizing in the line.

Ball valves are preferred to provide a positive shut-off with negligible effects on chamber volumes. Flexible drives may be used in order to operate the valves. Piston 15 should be adjusted with a locking device to bottom out before bellows 12 is fully compressed.

CALIBRATION

Calibration of the apparatus according to the present invention depends upon the effective volume of measuring chamber 20. The volume of tubing between sampling chamber 10 and measuring chamber 20 must be taken into account.

The stroke of expansion chamber piston 36 is adjusted to set the amount of air in and to reduce pressure in measuring chamber 20. Pressure within measuring chamber 20 is restored to atmospheric pressure when a sample is injected. The value of the reduced pressure depends upon a desired vapor/liquid ratio, the dead volume in bellows 32, the volume of measuring chamber 30 and the volume of tubing 82. ASTM D-323 requires a vapor to liquid volume ratio of approximately 4 to 1. Also, in the present invention, the volume of air withdrawn from measuring chamber 20 into expansion chamber 30 must correspond closely to the volume of the liquid sample to be introduced into measuring chamber 20 from sample chamber 10.

During the expansion step, expansion chamber 30 must remove an amount of air, measured as dry air, from measuring chamber 20 such that the air remaining in measuring chamber 20 will return to exactly one atmospheric pressure if that is compressed by a volume equal to one liquid sample. Even though the composition of the air withdrawn from measuring chamber 20 by bellows 32 has a higher moisture content at the beginning of expansion stroke than at the end, it can be shown that bellows 32 removes an amount of air, measured as dry air, that is sufficiently constant regardless of the moisture content of measuring chamber 20, within a reasonable range of possible values.

OPERATION OF PREFERRED EMBODIMENT

A preferred method of measuring RVP according to the present invention is illustrated by the chart of FIG. 2. After a sample can 60 has been attached to sample can adaptor 62, after valves 92 and 70 have been opened by manipulation of knobs 95 and 96 respectively, and after sample can 60 and sample 61 are sufficiently chilled, a sequence of operations according to the present invention may begin.

As shown in FIG. 2, in Step 1, valve 310 is operated to direct air through tubing 114 and valve 83 into expansion chamber 30 for approximately 2 seconds. Next, valve 81 is opened to allow air to pass from expansion chamber 30 to measuring chamber 20. The air passes out of measuring chamber 20 thorugh valves 80, and drain conduit 108 to flush chambers 20 and 30. Air also leaves chamber 20 through valve 79, line 78, valve 77, line 76 and valve 75 to flush through chamber 10 and out valve 74, line 73, valve 72 and drain line 102. After about 7 seconds, the valve 80 is closed so that air supply to chambers 20 and 30 can only flow through valve 79.

Next, valve 310 is operated to connect chamber 30 with vent conduit 112 so that air is no longer flushed through chambers 10, 20 and 30. Furthermore, valve 81 is closed, disconnecting chamber 30 from chamber 20, and valve 80 is opened, connecting chamber 20 to drain conduit 108, and valve 75 is closed, disconnecting chamber 10 from chamber 20.

Next, sample chamber 10 is flushed three times with a liquid material to be tested and measuring chamber 20 is flushed three times alternately with water and air in preparation for the measurement of RVP. For the three flushings, valve 90 is opened, permitting air to pass from supply line 100 through valve 92 above material 61 and thereby facilitating material 61 to flow through valve 70. Valve 72 is operated to connect sample can 60 to chamber 10. Bellows 12 is drawn down, pulling a sample of material from can 60 into sample chamber 10. Valve 90 closes. Valve 72 connects sample chamber 10 with drain conduit 102. Next, bellows 12 again rises to expel the sample from chamber 10 through drain conduit 102.

Contemporaneously with the flushing of chamber 10, chamber 20 is flushed with water and air. Valve 77 is operated to connect chamber 20 with valve 305. Next, valve 306 is operated to connect valve 77 with valve 305 and valve 305 is operated to allow water to flow through alves 306, 77, and 79 into measuring chamber 20 and out through valve 80 and drain conduit 108. Motor 313 is turned on followed by closing of valve 80 so that water is agitated within chamber 20. Valve 80 is again opened so that the water drains from chamber 20 through drain conduit 108. Next, valve 305 is switched from water to air so that measuring chamber 20 is flushed with air. Motor 313 is turned off.

After the third flushing cycle, the RVP of a sample is measured. Valve 90 is opened, valve 72 is operated to connect sample can 60 with chamber 10 and then bellows 12 is drawn down to pull liquid material 61 from can 60. Valve 74 is closed to disconnect sample can 60 from sample chamber 10 at the same time that valve 90 is closed to shut off air supply to chamber 60 and valve 72 returns to its normal position.

Valve 81 is opened to connect measuring chamber 20 with expansion chamber 30 and motor 313 is turned on. Next, valve 83 is closed to disconnect chamber 30 from vent conduit 112, valve 80 is closed to disconnect chamber 20 from drain conduit 108 and valve 79 is closed to disconnect measuring chamber 20 from sample conduit 78. At this point, measuring chamber 20 and expansion chamber 30 are connected through valve 81 and constitute a unitary volume. Next, bellows 32 is raised, in order to expand the combined volume of chambers 20 and 30, followed by the closing of valve 81, which isolates measuring chamber 20 so that a reduced pressure is maintained. Simultaneously, expansion chamber 30 is vented through drain conduit 112 by opening valve 83 and compressing bellows 32.

Valve 75 opens contemporaneously with the falling of bellows 32. Next, valve 79 opens and bellows 12 rises, forcing the sample from sample chamber 10 through conduits 76 and 78 and into measuring chamber 20. Meanwhile, motor 313 is turned on so that entry of sample into measuring chamber 20 is accompanied by shaking of chamber 20.

Valve 79 closes, trapping the sample in chamber 20. The sample is shaken for three minutes so that equilibrium is attained, after which the RVP of the sample is measured. Valve 74 is opened in preparation for a new measurement cycle.

At the end of the three-minute measurement period, motor 313 is turned off and valves 80 and 81 are opened so that the sample drains from chamber 20 through drain conduit 108.

While the present invention has been described in terms of a preferred embodiment, further modifications and improvements will occur to those skilled in the art. For example, motor 313 may be replaced by a pneumatic shaker.

We desire to be understood, therefore, that this invention is not limited to the particular form shown and that we intend in the appended claims to cover all such equivalent variations which come within the scope of the invention as claimed.

What is claimed is:

1. An apparatus for measuring the Reid Vapor Pressure of a liquid hydrocarbon material comprising:
   first compartment maintained at a substantially fixed temperature about the range of 32° F. to 40° F.;
   a second compartment maintained at a substantially fixed temperature of about 100° F.;
   means, within said first compartment, for providing a sample of the liquid hydrocarbon material;
   a sample chamber within said first compartment;
   first means for connecting said means for providing a sample and said sample chamber;
   a measuring chamber within said second compartment;
   second means for connecting said sample chamber and said measuring chamber;
   an expansion chamber within said second compartment;
   third means for connecting said measuring chamber and said expansion chamber;
   means, associated with said measuring chamber, for measuring pressure; and
   means, coupled to said means for measuring pressure for providing an output indicative of the vapor pressure of a sample of the liquid hydrocarbon material.

2. The apparatus as recited in claim 1 wherein said expansion chamber comprises a bellows.

3. The apparatus as recited in claim 2 wherein said sample chamber comprises a bellows.

4. The apparatus as recited in claim 3 further comprising a sequence controller.

5. The apparatus as recited in claim 4 wherein said first and second means for connecting comprise valve and conduit systems and wherein said sequence controller directs operation of said valve and conduit systems.

6. The apparatus as recited in claim 5 further comprising air and water input systems and fourth means for connecting said input systems to said sample chamber and to said measuring chamber in order to prepare said sample and measuring chambers for measurement of said sample.

7. The apparatus as recited in claim 6 wherein said input systems are connected to said sample chamber and said measuring chamber, in a sequence determined by said sequence controller in order to purge said sample container, said measuring chamber and said second means for connecting.

8. The apparatus as recited in claim 7 wherein said input systems are connected to said sample and said measuring chambers in sequence by said sequence controller in order to provide water saturated air in preparation for measurement of the vapor pressure of said sample.

9. The apparatus as recited in claim 8 wherein said means for providing a sample comprises a sample can removably connected to said first means for connecting.

10. A method for measuring Reid Vapor Pressure of a liquid hydrocarbon material comprising the steps of:
    filling a sample chamber at a temperature within the range of about 32° F. to about 40° F. with a sample of the liquid hydrocarbon;
    preparing a measuring chamber at about 100° F. and atmospheric pressure;
    reducing the pressure of and the amount of air within said measuring chamber so that, after introduction of said sample, air within said measuring chamber is in an appropriate amount and at an appropriate pressure by
    (a) connecting said measuring chamber to an expansion chamber,
    (b) expanding said expansion chamber, and
    (c) disconnecting said measuring chamber from said expansion chamber;
    transferring said sample of the liquid hydrocarbon from said sample chamber to said measuring chamber; and
    measuring vapor pressure within said measuring chamber, after equilibration, as the Reid Vapor Pressure of said sample.

11. The method as recited in claim 10 wherein said expanding step is effected by moving a bellows within said expansion chamber.

12. The method as recited in claim 11 wherein said filling step is effected by moving a bellows within said sample chamber.

13. The method as recited in claim 12 further comprising the step of shaking said sample within said measuring chamber in order to effect said equilibrium.

14. The method as recited in claim 12 further comprising the step of producing water-saturated air at 100° F. and atmospheric pressure in said measuring chamber.

15. The method as recited in claim 14 wherein said sample has a volume, $V_S$, wherein said measuring chamber has a volume, $5 V_S$, and wherein said expanding step comprises the step of adjusting expansion of said expansion chamber so that said total volume of said measuring and expansion chambers is equal to 6.25 times the volume of said sample within said measuring chamber.

* * * * *